United States Patent
Green et al.

(10) Patent No.: US 6,577,958 B1
(45) Date of Patent: Jun. 10, 2003

(54) SURVEILLANT CONCURRENT ENGINEERING PROCESS TOOL FOR ENVIRONMENT RENDERING (SCEPTER) FOR RESIN FLOW MONITORING IN COMPOSITES

(75) Inventors: William H. Green, Owings Mills, MD (US); Shawn M. Walsh, Baltimore, MD (US); Dale R. Shires, Bel Air, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 161 days.

(21) Appl. No.: 09/616,892

(22) Filed: Jul. 14, 2000

Related U.S. Application Data

(60) Provisional application No. 60/150,406, filed on Aug. 23, 1999.

(51) Int. Cl.[7] ................................................. G01F 1/00
(52) U.S. Cl. .......................................... 702/45; 324/649
(58) Field of Search ............................. 702/45; 324/649

(56) References Cited

U.S. PATENT DOCUMENTS 5,097,432 A * 3/1992 Harada et al. ............... 324/649
5,210,499 A    5/1993 Walsh ......................... 324/649

OTHER PUBLICATIONS

Development and Testing of an Interface for Real–Time Visualization of Resin Flow in Composites, William Green, Dale Shires and Shawn Walsh, ARL–TR–1784 Sep. 1998.

* cited by examiner

Primary Examiner—John Barlow
Assistant Examiner—Anthony Dougherty
(74) Attorney, Agent, or Firm—Paul S. Clohan, Jr.; William W. Randolph

(57) ABSTRACT

The invention presents a new methodology to monitor and display the resin flow during fabrication of organic matrix composite laminates in real-time or near real-time and includes data acquisition, remote data distribution, flow analysis and reconstruction, and flow visualization. The data acquisition apparatus is based on SMARTweave technology, as described in U.S. Pat. No. 5,210,499, which provides the location of points on the flow front as a function of time by using voltage measurements. However, the methodology will monitor and display the resin flow if the location and time information is acquired using modified SMARTweave or different apparatus.

5 Claims, 3 Drawing Sheets

SURVEILLANT CONCURRENT ENGINEERING PROCESS TOOL FOR ENVIRONMENT RENDERING (SCEPTER) FOR RESIN FLOW MONITORING IN COMPOSITES

This application is a continuation of provisional application No. 60/150,406 filed Aug. 23, 1999.

RIGHTS OF THE GOVERNMENT

The invention described herein may be manufactured, used, and licensed by or for the United States Government for governmental purposes without the payment to us of any royalty thereon.

BACKGROUND OF THE INVENTION

Liquid Composite Molding (LCM) processes, such as Resin Transfer Molding (RTM) and Structural Reaction Injection Molding (SRIM), are manufacturing methods for fabricating high-strength, high-volume composite parts. Composite parts are still generally cured in autoclaves, ovens, or presses using empirically based "recipe" cures. Most previous attempts to solve the problems inherent in recipe cures have concentrated on reducing batch-to-batch variations in raw materials and pre-production "proof" processing to accommodate those variations. This approach has been only moderately successful, and not optimally cost effective. Current studies of multi-regional flow in LCM processes do not determine actual flow front location using real-time sensor data during the process. These studies simulate the resin flow using material and process parameters, including permeability, injection pressure, vacuum pressure, and port and vent locations. They often record the resin flow on the surface of the composite on video to compare to simulations.

The present invention accurately determines the actual flow area and location of the flow front in a short time relative to the speed of the flow front. It is not a simulation of the flow using material and process parameters before actual fabrication. Thus, the actual state of fill of the composite in relation to the ports and vents in the mold cavity is known throughout the fabrication process. The present invention can also determine flow front velocity. Since location, speed, and direction fully describe flow in the immediate future, the present invention can be used as the basis of a control methodology capable of modifying the actual condition of the material in real-time or near real-time as it is being processed. Intelligent process control would respond relatively quickly to analysis results to modify flow parameters, e.g., port injection pressure, activation/shut off of injectors, etc.

SUMMARY OF THE INVENTION

Accordingly, it is an object of the present invention to provide an apparatus and associated methodology to monitor and display the resin flow during fabrication of organic matrix composite laminates.

The foregoing object is achieved by integration of novel sensor technology, network-based data acquisition, fast finite element based reconstruction (smoothing) and contouring algorithms, and scientific visualization tools. The invention uses a robust combination of data analysis and data visualization techniques to accurately show the entire composite laminate and the flow in the laminate in an easily understood three dimensional display. The invention can display the flow area or the flow front. Either mode of display is easily interpretable without requiring any detailed knowledge of the acquisition, reconstruction, and visualization methodology.

BRIEF DESCRIPTION OF THE DRAWINGS

The invention will be better understood, and further objects, features, and advantages thereof will become more apparent from the following description of the preferred embodiment, taken in conjunction with the accompanying drawings in which.

DETAILED DESCRIPTION OF THE PREFERRED EMBODIMENTS

Figure 1C:
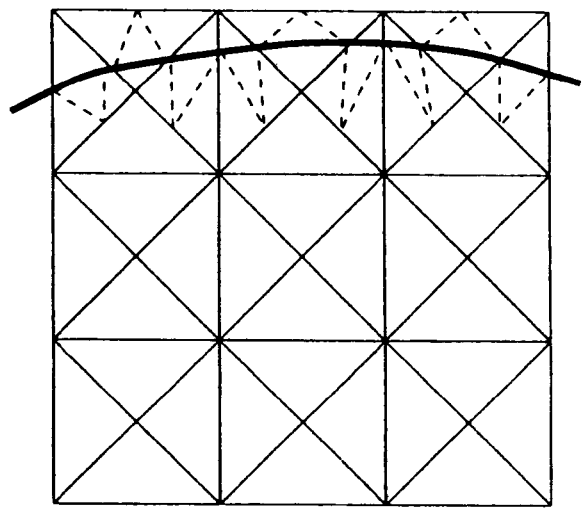
FIGS. 1a, 1b, 1c illustrates "Coarse" 2D finite element mesh with moving flow front using four-element refinement.

The SMARTWeave system (U.S. Pat. No. 5,210,499 hereby incorporated by reference) has the potential to collect data from everywhere in a composite preform, and thus determine the current location of the global flow front. The SMARTWeave system produced a simple yet effective monitoring system. The multiplexed data collected at the grid overlap points, or sensor locations, is interpreted by customized National Instruments LabVIEW software running on a personal computer (PC). Based on predetermined thresholds, voltages at the sensors were indicative of whether or not resin had filled the sensor. The user was presented a graphical, two-dimensional (2D) representation of the preform that was colored based on voltage readings from the sensors or whether or not voltage thresholds had been exceeded. However, this visualization tool was constrained in two ways. First, only 2D cases could be fully visualized, and second, the 2D representation was constructed using rectangles delimited by the grid tows. This always produced a flow front with 90-degree steps. Of course, more tows could be added to decrease this effect, but a great advantage of the SMARTWeave system is that flow can be determined where there are no sensors by analyzing sparse sensor data. Flow in these areas could not be accurately shown with the "blocky" output from the early, PC-based, visualization tool. Also, adding more tows becomes impractical at a certain point.

In order to visualize three-dimensional (3D) experiments, the present invention was developed to transfer the data from the monitoring computer to a Silicon Graphics Incorporated (SGI) workstation in near real time. The SGI computer system was chosen for several reasons. Most importantly, the SGI has graphics hardware and software that allows users to easily render and manipulate 3D objects. This is done using Open Inventor, which is an object-oriented 3D toolkit based on Open GL (Graphics Library). Open GL is the interface by which the graphics hardware is controlled. Secondly, the OSF/Motif programming toolkit, which is built on top of the X11 code used for the UNIX windows environment on the SGI, is used to implement user interface components, such as menus, scroll bars, message boxes, and buttons. Mechanisms exist that incorporate the Motif and X11 components with the Open Inventor components.

Remote acquisition of process or laboratory data in real-time or near real-time is a powerful application that Internet access provides. Routines were written on the PC and on the SGI to allow communication between the two over existing TCP/IP network channels. The LabVIEW software on the PC has routines specifically for TCP/IP network communication. These routines were used to allow the PC user to input the Internet address of the SGI workstation and the port to which it should connect. The PC then collects data at user set intervals and sends bursts of data over the network to the SGI workstation. The SGI workstation could have been used as the data acquisition device. However, an effective and highly portable PC-based data monitoring system existed, allowing dedication of the SGI to data analysis and flow rendering. The PC was fitted with a network card. Code was written for the SGI that allows the user to specify a TCP/IP socket, which will act as a listener. This is done in the SGI user interface for the SMARTWeave monitoring system. Most workstations in the SGI family are network-ready. This system of data acquisition and transfer has two advantages. It does not require specialized connectors to interface the two computers and it allows for distributed data collection and visualization.

Any number of sensors can be created utilizing the SMARTWeave system. However, it is desirable to use as few sensors as possible to collect data without losing information necessary for correctly determining flow front location. Currently, the capability exists to visualize sensor activity in near real-time. Sensor points are turned on when they are filled as resin flows through the preform. However, it is useful to know where the flow front is between the sensor points. Off-line capability has been developed to quickly reconstruct the flow front based on sensor locations and sensor activation (on) times. In the 2D case, the reconstruction (smoothing) algorithm uses a triangular, quadratic, and computationally efficient element possessing 9 degrees-of-freedom (dof) to locate the flow front in time based on a finite element model. The response of this particular smoothing element (in finite element notation) is dictated by three separate components and can be summarized as:

$$[K^e]\{u^e\} = ([K_\epsilon^e] + [K_\alpha^e] + [K_\beta^e])\{u^e\} = \{f^e\}$$

where $K_\epsilon$, $K_\alpha$, and $K_\beta$ symbolically represent the contributions of least square error, gradient control, and curvature constraint, respectively, and $u^e$ represents the nodal dof. The interpolation function $U^e$ within an element is written:

$$U^e = [N]\{u^e\}$$

where N are the element shape functions. The function $U^e$ is related to the piecewise representation of the smooth function $U(x, y)$, defined in region $\Omega$, contained in Euclidean 2D space, by:

$$\Phi(U) = \sum_{e=1}^{N_e} \Phi^e(U) = \sum_{e=1}^{N_e} \left\{ \frac{1}{2N_d^e} \sum_{i=1}^{N_d^e} \omega_i [U^e(x_i, y_i) - u_i]^2 + \frac{\alpha}{2} \int_{\Omega_e} [(U_{,x}^e - \theta_x^e)^2 + (U_{,y}^e - \theta_y^e)^2] d\Omega + \frac{\beta}{2} \int_{\Omega_e} [(U_{,xx}^e)^2 + 2(U_{,xy}^e)^2 + (U_{,yy}^e)^2] d\Omega \right\}$$

where $N_e$ is the number of finite elements, $N_d^e$ is the number of data points falling within an element's space, $u_i = u(x_i, y_i)$ is an arbitrary representative data set, $U_{,ij}$ denotes partial differentiation, and $U^e$, $\theta_x^e$, and $\theta_y^e$ are functions restricted to an element's domain. The data weighting constant, derivative or gradient constraint constant, and the curvature constraint constant are represented by $\omega$, $\alpha$, and $\beta$, respectively. In this case, the data set $u_i$ is time. An expression for $K_\epsilon$, $K_\alpha$, $K_\beta$, and $f^e$ results from the minimization of the functional in the third equation with respect to the nodal dof, $\partial \Phi/\partial u = 0$, and combination with the second equation. This is one model that can be used to obtain time-dependent nodal data from sensor data. The present invention does not require this particular model as other models can be used to obtain the necessary nodal data.

The algorithm determines the time solution for every node in the finite element model given the times sensors are activated. Thus, sparse data from a small number of sensors is analyzed to get data over the entire finite element model, which gives the resin flow front at discrete time intervals. Some elements will have all their nodes in the filled (on) state, some will have all their nodes in the unfilled (off) state, and some will have only one or two nodes in the filled state. Any element that has only one or two nodes on is considered to be partially filled with resin. A linear first approximation contouring methodology is used to determine what areas of partially filled elements should be considered filled. Contouring is generally not necessary for a relatively fine finite element mesh. However, since contouring is only applied to partial (filled) elements it is only applied along the flow front. Contouring a relatively small number of partial elements can take less time than smoothing a very fine mesh in order to avoid contouring, since solving for such a mesh can be computationally intensive.

Figure 1B:
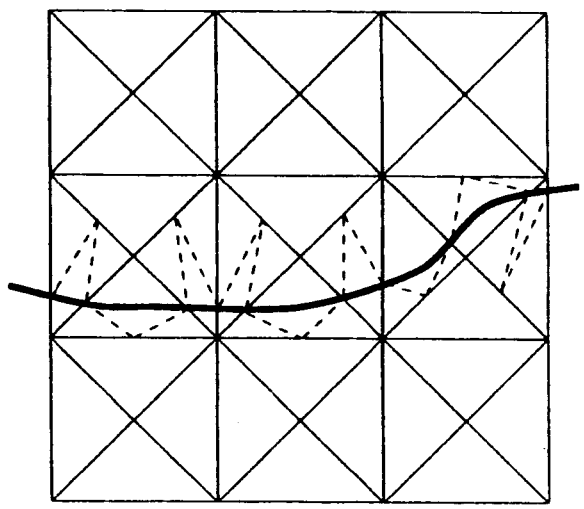
Figure 1A:
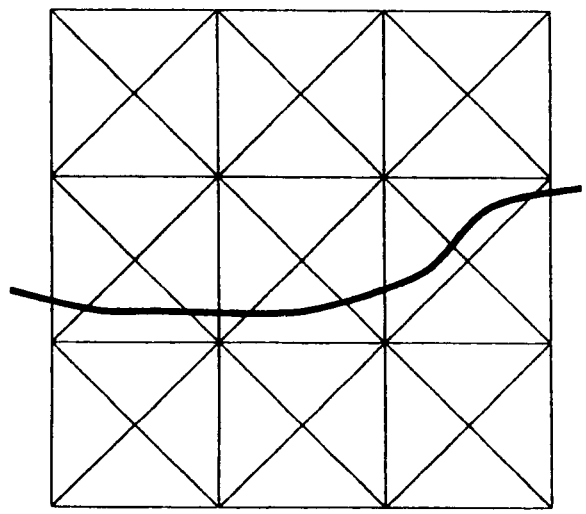
Figure 2B:
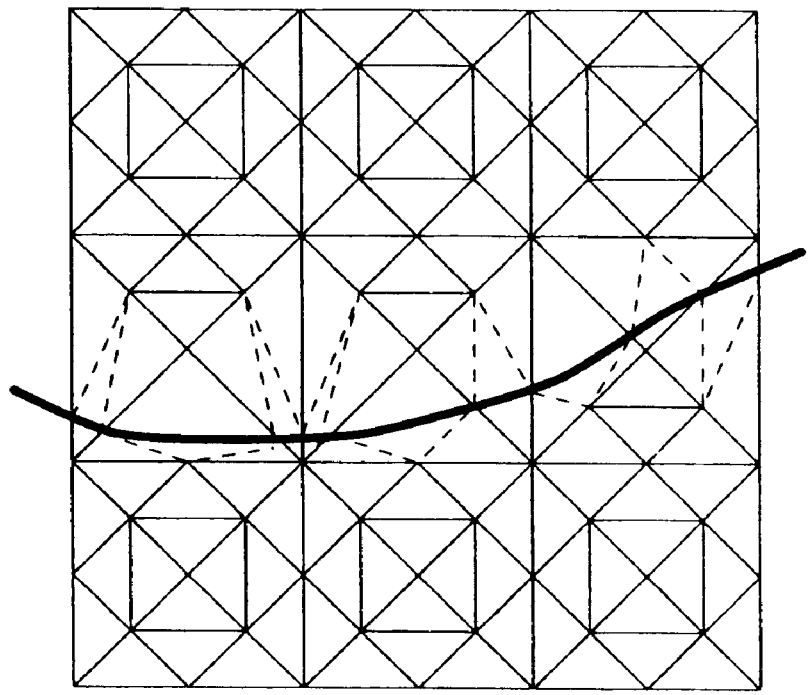
FIGS. 2a, 2b illustrates "Fine" 2D finite element mesh with moving flow front using element repositioning by node relocation.
Figure 2A:
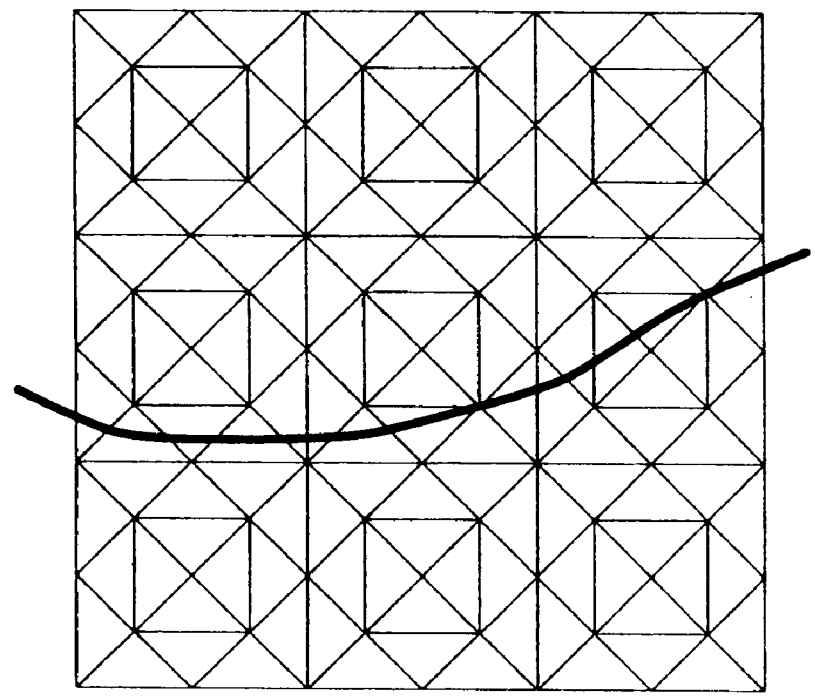

Consider the following figures. FIG. 1a is a 2D finite element mesh, or grid, with the flow front moving from left to right. FIG. 1b is the same grid with four-element refinement applied to the partial elements along the flow front. Four element refinement is the process of creating four new elements that collectively describe the same area in space as the partial element they temporarily replace such that the flow front is delineated, or contoured, in the area of the partial element. The flow front is contoured in the partial element because each temporary new element is either completely in the flow region or completely out of the flow region. FIG. 1c shows four element refinement applied to the flow front later in time. The 12 elements down the middle of the grid have been reset to their original size and their original position. These elements have gone from partial elements to filled elements, whereas the 12 elements to their right have gone from empty elements to partial elements. As the flow front moves through the grid, nodes and elements are added and removed from it as necessary to contour partial elements. FIG. 2a is a refined grid with the flow front moving from left to right. FIG. 2b is the same grid with elements repositioned along the flow front, but no further refinement. Nine elements are dynamically replaced with 36 elements in FIGS. 1b and 1c. An original finer mesh is used in FIGS. 2a and 2b with simple element repositioning by node relocation. In order to use as coarse a grid as possible and minimize processing time, dynamic mesh refinement (DMR) as shown in FIGS. 1b and 1c is used for flow front contouring.

Flow visualization and modeling in various areas of industry and research (e.g., textile materials, satellite images, virtual environments, etc.) is becoming increasingly important. Realistic and accurate representation of objects or images is often necessary to meet design or system requirements. Open Inventor is designed to create and display 3D objects. All of the information about an object, such as its size, position, color, etc. is stored in a data structure known as a scene database. This scene database visually looks like a tree structure. When the scene database, or scene graph, is displayed or rendered, it is traversed top-down, left-to-right. For any object, the design is logical and can be easily understood by traversing the scene graph. Finite element mesh geometry of an object can be formatted into an Open Inventor scene graph. The flow visualization interface quickly reads and formats a NASTRAN (finite element) file into an Open Inventor scene graph, which renders the object described by the file. However, any data file specifying nodes and nodal connectivity can be used. The NASTRAN file is generated from Parametric Technology Corporation Pro/ENGINEER computer-aided design (CAD) software. The same finite element mesh used for rendering the object is used for smoothing and contouring, and also for performing flow simulations. Thus, the mesh is not made too fine or too coarse. If the mesh is too fine it results in slow rendering and contouring, but very good simulations. If the mesh is too coarse it results in bad simulations, but fast rendering and contouring.

The time to complete smoothing, contouring, and rendering tasks is small relative to the speed of the flow front so that the flow front is accurately displayed when new sensor data is received. If the computation time required to complete these tasks is too large the displayed flow front will lag in time behind the actual flow front. The visualization interface allows the user to turn off smoothing and contouring in order to view the sensor state only. The interface can also apply only smoothing to sensor data. In this case, the time solution for each node in the mesh is compared to the current time, and any node with time less than or equal to the current time is a filled node. The interface uses color shading around nodes to distinguish between filled and empty nodes. However, shading by node gives the flow front a step-like, unsharp edge. This method gave better results than the PC-based "blocky" display, but still did not clearly delineate the flow front. This was the impetus to develop element shading with DMR for contouring, which gives the flow front a well-defined edge without step-like contours between nodes. This approach shows the entire flow. An approach was also developed to show only the flow front, in which nodes on the front are marked by spheres and connected using straight-line segments.

SCEPTER is the result of the novel integration of several different hardware and software methodologies. It is a unique, powerful, flexible, and user friendly tool for visualization of resin flow in organic matrix composite laminates in real-time or near real-time. SCEPTER has been used to successfully monitor resin flow in a variety of flow experiments. This includes flow in single material flat panels, bi-material flat panels, and panels with rectangular and oval inserts, including ceramic inserts.

Figure 3:
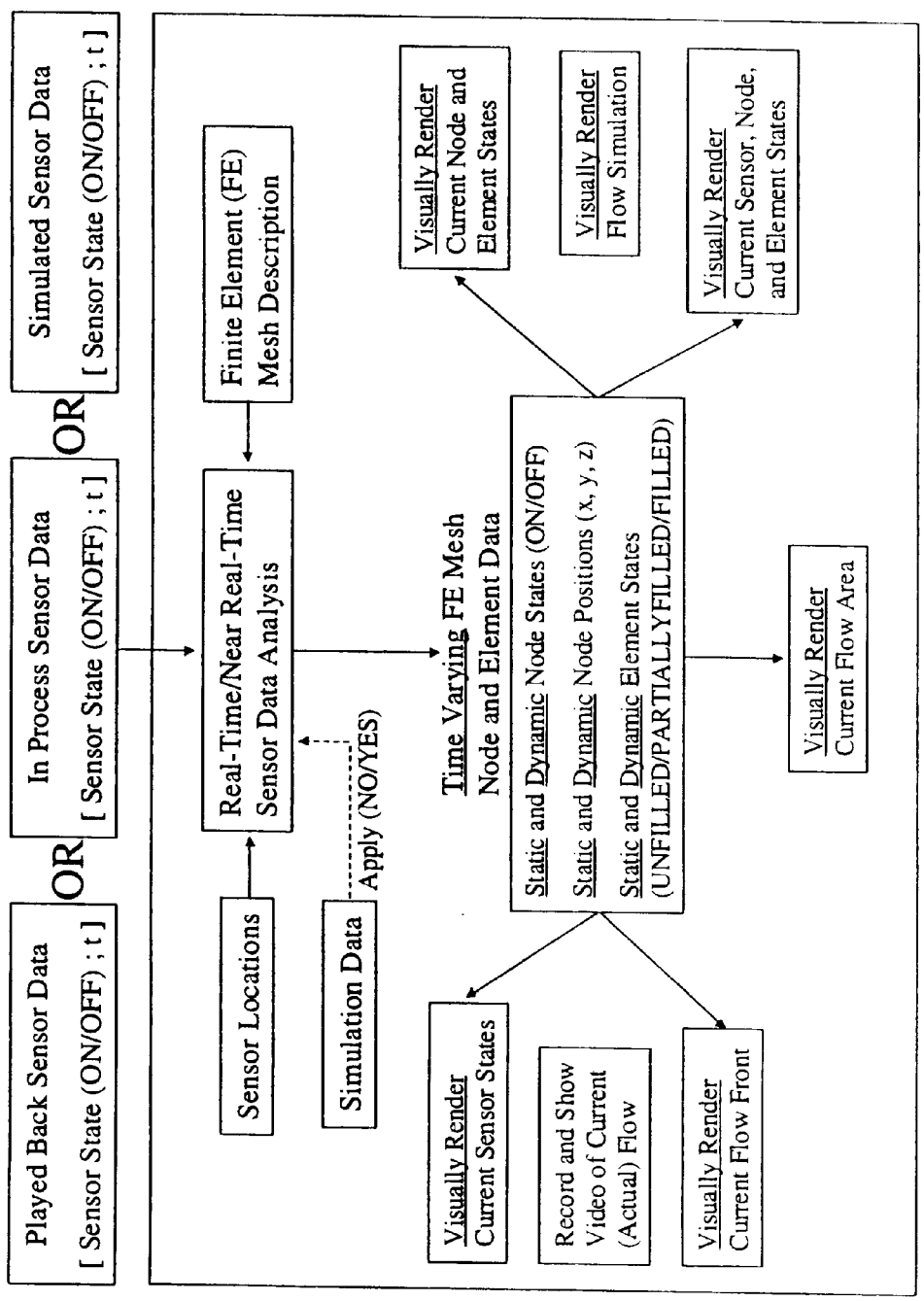
FIG. 3 is a schematic diagram of the present invention.

A summary schematic block diagram of the SCEPTER system is given in FIG. 3. It shows the multi-functionality of the SCEPTER system and its capability to provide data in various ways, including live video, simulated data, and real-time/near real-time flow data in different forms.

SCEPTER has also been used to successfully monitor resin flow in a thinner version of the significantly more complex XM194 Gun Mount Shield. Different resin port systems have been used in the experiments, including center point injection, corner point injection, center line injection, edge line injection, and staggered double or triple line injection. SCEPTER has produced accurate flow reconstruction results in a variety of flow experiments, which when shaded by element and contoured using dynamic mesh refinement resulted in well defined flow front boundaries in good agreement with video tape recordings.

It will be readily seen by one of ordinary skill in the art that the present invention fulfills all of the objects set forth above. After reading the foregoing specification, one of ordinary skill will be able to effect various changes, substitutions of equivalents and various other aspects of the present invention as broadly disclosed herein. It is therefore intended that the protection granted hereon be limited only by the definition contained in the appended claims and equivalents thereof.

Having thus shown and described what is at present considered to be the preferred embodiment of the present invention, it should be noted that the same has been made by way of illustration and not limitation. Accordingly, all modifications, alterations and changes coming within the spirit and scope of the present invention are herein meant to be included.

We claim:

1. A method for real-time or near real-time visualization of resin flow in composites comprising the steps of:
    data acquisition from sensors located within the resin flow;
    remote data distribution;
    flow analysis and reconstruction, comprising a fast finite element based reconstruction and contouring algorithm, which includes a smoothing algorithm using a triangular, quadratic, and computationally efficient element possessing nine degrees-of-freedom to locate the flow front; and
    flow visualization.

2. The method of claim 1, further comprising the steps of:
    determining a time solution for every node in the finite element model given the times the sensors are activated;
    analyzing the sensor data to obtain data over the entire finite element model to obtain resin flow front at discrete time intervals; and
    contouring the resin flow front.

3. The method of claim 2, wherein the step of data acquisition from sensors located within the resin flow comprises the steps of:
    pumping a resin material into a resistance monitoring device having electrically conductive sensor threads arranged in a non-intersecting, grid-like configuration so as to create a plurality of sensor gaps;
    allowing the pumped resin to advance through the grid-like configuration and sensor gaps of the resistance monitoring device;
    obtaining and sending an electrical signal received from the sensor gaps as the pumped resin reaches the sensor gaps to a signal interpreting apparatus with a data storage and presentation means.

4. The method of claim 3, herein the step of remote data distribution comprises the step of:
    utilizing a network for communication between the data storage and presentation means and a graphics hardware and software device allowing a user to render and manipulate three-dimensional objects.

5. An apparatus for real-time or near real-time visualization of resin flow in composites, comprising:
    sensors located within the resin flow for data acquisition;
    means for remote distribution of the acquired sensor data;
    means for flow analysis and reconstruction of the acquired sensor data comprising a fast finite element based reconstruction and contouring algorithm which includes a smoothing algorithm using a triangular, quadratic, and computationally efficient element possessing nine degrees-of-freedom; and
    means for visualizing the analyzed and reconstructed resin flow.

* * * * *